United States Patent
Hendriks et al.

(10) Patent No.: US 12,298,299 B2
(45) Date of Patent: May 13, 2025

(54) PREDICTING THE ONSET OF A PHYSIOLOGICAL CONDITION OF A SUBJECT USING A DIGITAL BIOPHYSICAL MODEL

(71) Applicant: KONINKLIJKE PHILIPS N.V., Eindhoven (NL)

(72) Inventors: Cornelis Petrus Hendriks, Eindhoven (NL); Eduard Gerard Marie Pelssers, Panningen (NL); Valentina Lavezzo, Heeze (NL); Murtaza Bulut, Eindhoven (NL); Lieke Gertruda Elisabeth Cox, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1347 days.

(21) Appl. No.: 16/844,517

(22) Filed: Apr. 9, 2020

(65) Prior Publication Data

US 2020/0340980 A1    Oct. 29, 2020

Related U.S. Application Data

(60) Provisional application No. 62/837,359, filed on Apr. 23, 2019.

(51) Int. Cl.
*G01N 33/50* (2006.01)
*B01L 3/00* (2006.01)
(Continued)

(52) U.S. Cl.
CPC ........ *G01N 33/5082* (2013.01); *B01L 3/5027* (2013.01); *G16H 30/40* (2018.01);
(Continued)

(58) Field of Classification Search
CPC .............. B01L 3/5027; G01N 33/5008; G01N 2800/122; G01N 33/5014; G01N 33/5061;
(Continued)

(56) References Cited

U.S. PATENT DOCUMENTS

2015/0004077 A1* 1/2015 Wikswo ................. C12M 29/10
422/502
2017/0065976 A1* 3/2017 Varma ................... F04B 49/065
(Continued)

OTHER PUBLICATIONS

Dr. Vanessa Diaz in https://www.wareable.com/health-and-welbeing/doctor-virtual-twin-digital-patient-ucl-887 retrieved on internet on Oct. 29, 2018.
(Continued)

*Primary Examiner* — Jill A Warden
*Assistant Examiner* — Dwayne K Handy

(57) ABSTRACT

A system for predicting the onset of a physiological condition of a subject combines an in-vitro subject model having input parameters relating to actual or predicted external stimuli to which the subject is or may be exposed and an in-silico model. The in-vitro model outputs subject-specific parameters which are not being monitored, or cannot be monitored, in-vivo. The in-silico subject model uses subject-specific parameters to predict the response of the subject to the actual or predicted external stimuli and thereby predict an onset of a physiological condition of the subject.

11 Claims, 1 Drawing Sheet

(51) Int. Cl.
G16H 30/40 (2018.01)
G16H 50/20 (2018.01)
G16H 50/30 (2018.01)
G16H 50/50 (2018.01)
G16H 70/40 (2018.01)

(52) U.S. Cl.
CPC ............. *G16H 50/20* (2018.01); *G16H 50/30* (2018.01); *G16H 50/50* (2018.01); *B01L 2300/0663* (2013.01); *G01N 2800/122* (2013.01); *G01N 2800/24* (2013.01); *G16H 70/40* (2018.01)

(58) Field of Classification Search
CPC ........... G01N 33/5064; G01N 33/5082; G16H 50/20; G16H 70/60; G16H 50/50
See application file for complete search history.

(56) References Cited

U.S. PATENT DOCUMENTS

| | | |
|---|---|---|
| 2017/0286572 A1 | 10/2017 | Dell'Anno et al. |
| 2018/0053346 A1 | 2/2018 | Comaniciu et al. |
| 2019/0106665 A1 | 4/2019 | Bahinski et al. |

OTHER PUBLICATIONS

Neal, M.L. et al., "Current progress in patient-specific modeling". Briefings in Bioinformatics, vol. 11, No. 1, 111-126. 1, 2009, vol. 2, pp. 111-126.

Benam, K.H. et al., 2017, "Human Lung Small Airway-on-a-Chip Protocol". Nature Methods, vol. 13, No. 2, Feb. 2016, pp. 151-160.

Koledova, A. "3D Cell Culture". Methods in Molecular Biology, (2017). Humana Press, New York, NY. Abstract.

Guo, H. et al., "A computational study of mucociliary transport in healthy and diseased environments", European journal of computational mechanics, (2017) vol. 26, No. 1-2, Abstract.

Chatelin, R. et al., (2017) "Numerical and experimental investigation of mucociliary clearance breakdown in cystic fibrosis" Journal of Biomechanics, vol. 53, pp. 56-63.

Paz, C et al., 2017, "Glottis effects on the cough clearance process simulated with a CFD dynamic mesh and Eulerian wall film model", Computer Methods in Biomechanics and Biomedical Engineering, vol. 20, No. 12, Abstract.

Paz, C. et al., 2017, "CFD transient simulation of the cough clearance process using an Eulerian wall film model", Computer Methods in Biomechanics and Biomedical Engineering, vol. 20, No. 2, 142-152.

De Backer, J.W. et al., 2008, "Flow analyses in the lower airways: Patient-specific model and boundary conditions", Medical Engineering & Physics 30 (2008) 872-879.

Bhatia, S.N., "Microfluidic organs-on-chip". Nature Biotechnology. vol. 32, No. 8, Aug. 2014.

Sturla, S.J. et al., "Systems toxicology: from basic research to risk assessment". Chemical Research in Toxicology (2014), 27, 314-329.

Knudsen, T.B. et al., "Future Tox II: In vitro data and In Silico models for predictive toxicology", Toxicological Sciences, 143(2), 2015, 256-267.

Jansen, K.A. et al., "A guide to mechanobiology: where biology and physics meet". Biochimica et Biophysica Acta 1853 (2015) 3043-3052.

* cited by examiner

PREDICTING THE ONSET OF A PHYSIOLOGICAL CONDITION OF A SUBJECT USING A DIGITAL BIOPHYSICAL MODEL

CROSS-REFERENCE TO PRIOR APPLICATIONS

This patent application claims the priority benefit under 35 U.S.C. § 119 (e) of U.S. Provisional Application No. 62/837,359 filed on Apr. 23, 2019, the contents of which are herein incorporated by reference.

FIELD OF THE INVENTION

This invention relates to uses of a digital model of a biophysical organism, by which is meant a set of data which provides a biophysical model of a physiological system or part of a physiological system. Such a model may be termed a digital twin.

BACKGROUND OF THE INVENTION

In many developed countries, the provision of healthcare is becoming increasingly strained. Some reasons for this include the growth of the population and increasing life expectancy. Unfortunately, although people live longer, the average age at which their health deteriorates to the point where regular medical care is required is not increasing accordingly, such that the ageing population is unwell for longer, which increases the pressure on the healthcare system, e.g. on medical practitioners, medical infrastructures such as hospitals, diagnostic equipment therein, and so on. Hence, rather than simply increasing medical resources, for which the financial resources may not be available, there exists a need to improve the efficiency of such healthcare systems.

A recent development is the so-called digital twin concept. In this concept, a digital representation (the digital twin) of a physical system is provided and connected to its physical counterpart, for example through the Internet of things as explained in U.S. 2017/286572 A1 for example. Through this connection, the digital twin typically receives data pertaining to the state of the physical system, such as sensor readings or the like, based on which the digital twin can predict the actual status of the physical system. In the case of electromechanical systems, this for example may be used to predict the end-of-life of components of the system, thereby reducing the risk of component failure as timely replacement of the component may be arranged based on its end-of-life as estimated by the digital twin.

Such digital twin technology is also becoming of interest in the medical field, as it provides an approach to more efficient medical care provision. For example, the digital twin may be built using imaging data of the subject, e.g. a patient suffering from a diagnosed medical condition as captured in the imaging data, as for instance is explained by Dr. Vanessa Diaz in https://www.wareable.com/health-and-wellbeing/doctor-virtual-twin-digital-patient-ucl-887 as retrieved from the Internet on 29 Oct. 2018.

Such a digital twin may serve a number of purposes. Firstly, the digital twin rather than the subject may be subjected to a number of virtual tests, e.g. treatment plans, to determine which treatment plan is most likely to be successful to the subject. This therefore reduces the number of tests that physically need to be performed on the actual subject.

The digital twin of the subject for instance further may be used to predict the onset, treatment or development of such medical conditions of the subject using the derived digital model. To this end, the subject may be fitted with one or more sensors that are connected to the digital twin. The digital twin typically uses sensor readings provided by the one or more sensors to assess the actual medical status of the subject, for example by developing a subject-specific model that is specific using the received sensor readings. For instance, such a model may be updated in one or more simulation runs until the updated model is a good fit to the received sensor readings.

One possible benefit is that the medical status of a subject may be monitored without the routine involvement of a medical practitioner, e.g. reducing periodic routine physical checks of the subject. Instead, only when the digital twin predicts a medical status of the subject indicative of the subject requiring medical attention based on the received sensor readings may the digital twin arrange for an appointment to see a medical practitioner to be made for the subject. This typically leads to a reduction in such appointments, thereby freeing up the medical practitioner to see other patients.

Another (additional or alternative) benefit is that the digital twin will facilitate the transition from reactive to proactive/preventative health care. This may initially involve even more doctor appointments, but hopefully also help to preserve or obtain a better health status.

Major medical incidents that the subject may be about to suffer may be predicted by the digital twin based on the monitoring of the subject's sensor readings, thereby reducing the risk of such incidents actually occurring. Such prevention avoids the need for the provision of substantial aftercare following such a major medical incident, which also alleviates the pressure on a healthcare system otherwise providing such aftercare.

The digital twin of a subject thus offers a clinician advanced interactive visualization and physical insights of relevant health information of the subject. Combining visualization with predictive models that provide projections of future health status and the outcomes of medical interventions results in personalized clinical decision support to improve diagnostics, treatment selection and interventions across the health continuum.

To enable the most accurate prediction, a challenge is to integrate biophysics models, data analytics, image processing and clinical expertise into the overall system.

A wide variety of models of (parts of) the human body exist. For example, the company BioDigital (Trade Mark) offers an interactive, 3D software platform to explore and visualize health information. It includes interactive 3D visualization of over 500 health conditions including heart disease, breast cancer, diabetes and more. This type of model is generic, so personalization is required to use such a model for building digital twins.

A typical workflow for creating and validating a 3D, subject-specific model is depicted in "Current progress in patient-specific modeling", by Neal and Kerckhoff, 1, 2009, Vol. 2, pp. 111-126.

A subject-specific biophysical model represents a complex physiological system. The model output depends on the quality and accuracy of the model input parameters, including the effect of subtle changes in these parameters. Examples of subject-specific model input parameters and quantification methods are:

Organ geometry from segmentation of a medical image (e.g. a CT scan);

Stiffness of soft tissues from quantitative ultrasound or magnetic resonance elastography; and Mucus viscosity from rheological measurements with mucus samples.

Known methods typically quantify the parameters only once (during a hospital visit), with the subject in a specific condition (e.g. lying in a scanner), and with limited resolution. For example, microscopic and functional properties of lining tissues are not captured. However, in a human body, these parameters may vary in time, may be sensitive to external stimuli (for example substances in inhaled air, food, blood), and may play a critical role with interactions with each other.

Therefore, a solution is needed to accurately determine the time and stimulus dependent model input parameters of a subject-specific biophysical model, in a non-obtrusive and non-invasive manner. It would be particularly desirable for the model to take account of changes in biophysical parameters which cannot easily be monitored over time (i.e. in-vivo).

SUMMARY OF THE INVENTION

The invention is defined by the claims.

According to examples in accordance with an aspect of the invention, there is provided a system for predicting the onset of a physiological condition of a subject, comprising:

an in-vitro subject model for modeling a tissue or organ type of a subject based on sample cells from the subject, the in-vitro model comprising input parameters relating to actual or predicted external stimuli to which the subject is or may be exposed, wherein the in-vitro model is adapted to output subject-specific parameters which are not being monitored, or cannot be monitored, in-vivo; and an in-silico subject model comprising subject-specific data which is relevant for the response of the particular subject to the subject-specific parameters, wherein the in-silico subject model is adapted to process the subject-specific parameters thereby to predict the response of the subject to the actual or predicted external stimuli and thereby predict an onset of a physiological condition of the subject.

This system combines in-vitro monitoring and in-silico analysis. The in-vitro monitoring is used to determine the response of a tissue or organ to a particular stimulus, which may be a drug which may be administered or external atmospheric or environmental conditions to which the subject may be exposed. The in-vitro model generates parameters which cannot or are not being monitored in-vivo. For example, some subjects may not be suitable for certain monitoring functions, so the in-vitro model may be used to predict the subject response. These parameters then supplement any actually monitored parameters of the subject when using the in-silico model to make predictions about the physiological condition of the subject. The physiological condition of the subject being predicted is for example a condition which requires medical intervention, or else preventative action to be taken.

This system enables more accurate modeling of the state of a subject and their need for imminent medical intervention.

The in-vitro subject model for example comprises a microfluidic system. Such systems are for example known as lab-on-a-chip systems, and they enable tissue samples to be exposed to different external conditions and to have their responses monitored.

The subject-specific parameters of the in-vitro subject model for example comprise one or more of:

a tissue thickness (e.g. indicating swelling or contraction);

an amount of stretching of tissue in response to an applied pressure;

a tissue stiffness; and a contraction power of muscle tissue.

These are examples of biophysical parameters which are not readily monitored in real time, but which have an impact on medical conditions and predictions.

The input parameters to the in-vitro subject model for example comprise one or more of:

exposure to a medicinal drug;

exposure to pollutants;

exposure to pressure;

exposure to particular concentrations of oxygen; and exposure to vibration.

These are external conditions to which the live subject may be exposed, and the in-vitro subject model provides a mechanism for modeling the response to these external stimuli.

A sensor arrangement may be provided for providing sensor information, or an input is provided for receiving sensor information from a remote source, wherein the sensor information is provided to the in-vitro subject model. The sensor information is for sensing conditions which affect the live subject, and the in-vitro model is controlled accordingly to model the response to those conditions.

The subject-specific data of the in-silico subject model for example comprises scan data. This may be ultrasound or magnetic resonance scan data, for example, The scan data may comprise one or more of:

the airway geometry; and the geometry of an organ of the subject.

The silico subject model is for example further adapted to derive treatment recommendations. Thus, the system can predict the onset of conditions which will need treatment as well as recommending early treatment interventions.

In one example, the physiological condition comprises an acute breathing event of a COPD patient.

In another example, the physiological condition comprises an allergic reaction.

The system may further comprise a user input for receiving an indication of the level of the physiological condition experienced by the subject. This enables the in-silico model to update in response to feedback from the subject relating to the accuracy of information provided by the system.

The invention also provides a method for predicting the onset of a physiological condition of a subject, comprising:

using an in-vitro subject model for modeling a tissue or organ type of a subject based on sample cells from the subject, the in-vitro model comprising input parameters relating to actual or predicted external stimuli to which the subject is or may be exposed;

outputting subject-specific parameters of the subject from the in-vitro subject model which are not being monitored, or cannot be monitored, in-vivo;

using an in-silico subject model comprising subject-specific data which is relevant for the response of the particular subject to the subject-specific parameters, wherein the in-silico subject model is used to process the subject-specific parameters thereby to predict the response of the subject to the actual or predicted external stimuli and thereby predict an onset of a physiological condition of the subject.

The subject-specific parameters of the in-vitro subject model for example comprise one or more of:
 a tissue thickness; and
 a contraction power of muscle tissue.

The input parameters to the in-vitro subject model for example comprise one or more of:
 exposure to a medicinal drug;
 exposure to pollutants;
 exposure to oxygen; and
 exposure to vibration.

The subject-specific data of the in-silico subject model for example comprises scan data, for example providing the airway geometry or the geometry of an organ of the subject.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
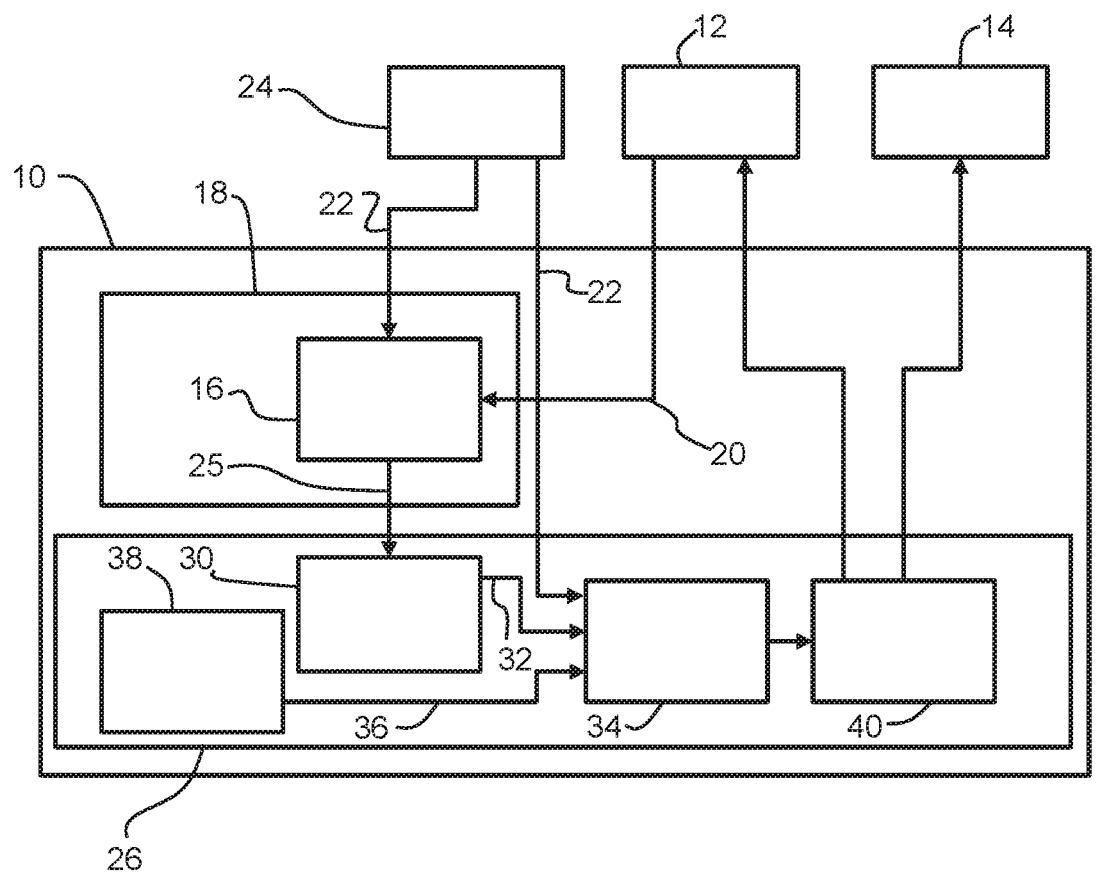
FIG. 1 shows a system for predicting the onset of a physiological condition of a subject.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system for predicting the onset of a physiological condition of a subject, which combines an in-vitro subject model having input parameters relating to actual or predicted external stimuli to which the subject is or may be exposed and an in-silico model. The in-vitro model outputs subject-specific parameters which are not being monitored, or cannot be monitored, in-vivo. The in-silico subject model uses subject-specific parameters to predict the response of the subject to the actual or predicted external stimuli and thereby predict an onset of a physiological condition of the subject. The system may also take account of historical information. For example, the build-up of stimuli may cause a response. For example, the exhaust of one passing car might not be a problem, but the cumulative exhaust of hundreds of passing cars might trigger a response. Similarly, brief exposure to smog may not be an issue whereas a smog which lasts for multiple days may trigger a response. These different conditions can thus be simulated over time.

The output of a subject-specific biophysical model depends on the quality of the input parameters. The input parameters may vary in time and may be sensitive to external stimuli. In order to quantify and validate the variation of input parameters, a subject-specific in-vitro model is used. The in-vitro model is stimulated with controlled conditions which represent variations in external parameters of the real subject. The input parameters of a computational in-silico model are adapted based on the response of the in-vitro model.

External stimuli to subjects may affect the behavior of particular tissues, in turn inducing a clinical disorder, i.e. the more generally the onset of a physiological condition. The in-silico model can calculate the effect of tissue behavior on this condition. However, in many cases it is very difficult, uncomfortable or impossible to measure the behavior of the tissue, not the least due the fact that the change in behavior of the tissue can take a long time. The in-vitro model is thus used to establish the relationship between the external stimuli and the behavior of particular tissues to avoid measuring the tissue characteristics on the subject. By coupling the in-vitro model results to the in-silico model, the in-vitro results serve as an input for the in-silico model, and consequently a versatile method for determining the effect of external stimuli on the clinical disorder can be predicted and measures can be taken to prevent or minimize the clinical disorder.

For example, environmental pollution may cause an inflammatory response in the lungs which in turn may cause an increase in the wall thickness of the small airways and accordingly a restricted airflow and a shortage in oxygen. It is difficult to impossible to measure the small airway wall thickness in subjects.

The system provides validated input parameters to enable accurate model predictions in the in silica system, with the possibility of real time updates of the model input parameters. The inputs may also otherwise not be accessible or only intrusively accessible.

FIG. 1 shows a system for predicting the onset of a physiological condition of a subject. The system may be implemented as a remote service 10 for providing information to a subject 12 (i.e. patient) and/or physician 14.

The system comprises an in-vitro subject model 16 hosted by a laboratory 18. The in-vitro model is used to model a tissue or organ type of the subject based on sample cells 20 obtained from the subject which function as a first input to the in-vitro model. The in-vitro model also receives input parameters 22 relating to actual or predicted external stimuli to which the subject is or may be exposed. These are received from an external source 24. The external source 24 may comprise sensors or a data resource (for example providing environmental conditions such as pollutant information) or a combination of these.

The in-vitro model is for example a microfluidic device containing a cell or tissue culture based on cells produced from subject's Induced Pluripotent Competent (IPC) stem cells, or cells harvested via biopsy and subsequent culturing.

Typical examples of cells used by the in-vitro model are from in-body lumen systems (blood vessels, airways), or from the skin.

Examples of cell or tissue types and the associated stimulus and response for a particular simulated issue and its associated medical condition are set out below:
 (i) Lung:
  Tissue: small airway wall: smooth muscle and epithelium
  Stimulus: smoke, air pollution, medication
  Response: swelling
  Simulated issue: air flow obstruction
  Associated medical condition: exacerbation in COPD, asthma (ii) Heart:
  Tissue: cardiac muscle
  Stimulus: electrical current (magnitude, timing)
  Response: contraction
  Simulated issue: cardiac output (pressure-volume loop)
  Associated medical condition: heart failure
(iii) Lung:
  Tissue: alveolar-capillary interface
  Stimulus: smoke, air pollution, medication
  Response: gas-transport between blood and air
  Simulated condition: gas exchange using cardiopulmonary model
  Associated medical condition: dyspnea, hypercapnia
(iv) Artery
  Tissue: artery wall: smooth muscle and endothelial cells
  Stimulus: cholesterol, medication
  Response: stiffness and plaque-buildup
  Simulated condition: blood flow obstruction
  Associated medical condition: atherosclerosis, heart attack
(v) Artery
  Tissue: artery wall
  Stimulus: fluid pressure
  Response: stretch (strain, creep)
  Simulated condition: vessel expansion (diameter, wall thickness)
  Associated medical condition: aneurysm rupture
(vi) Skin
  Tissue: skin cells (keratinocytes and fibroblasts)
  Stimulus: agents used to treat skin scars, burns, wounds
  Response: collagen production, cell differentiation (into myofibroblasts)
  Simulated condition: wound healing
  Associated medical condition: healing of scars, wounds, burns Often these cultures are called an organ-on-a-chip, although in almost all cases no functional organs are cultured but a collection of cells without topological functional features. Therefore recently a new name has been proposed: Micro Physiological System (MPS).

The in-vitro model can be used to determine the effect of external stimuli (examples of which are listed above) and time on the behavior or change of the cells or tissue (including immune response).

The in-vitro model outputs subject-specific parameters 25 which are not being monitored directly from the subject 12, or cannot be monitored, in-vivo. The in-vitro model represents a critical element of a biophysical model which is not accessible for "in-vivo" measurements with individual subjects, for example an in body lining tissue.

The in-silico subject model 26 is hosted by a computer system and comprises an algorithm which implements the digital twin concept described above. It includes subject-specific data which is relevant for the response of the particular subject to the subject-specific parameters 25.

The in-silico model is also provided with information about the external stimuli and/or time. Based on the subject-specific parameters (which provide information concerning the relationship between the tissue behavior and the stimuli), the subject-specific parameters can be taken into account.

Note that the in-vitro model and the in-silico model do not need to run simultaneously. The in-vitro model may be used to generate a set of output data, for subsequent use by the in-silico model.

The in-silico model uses first principles and geometrical information to calculate the level of a disorder in a quantitative manner. For example, a determined small airway wall thickness in combination with a subject's measured lung geometry may be used to calculate the increase in airflow obstruction or decrease in oxygen uptake by using biophysical computational tools.

The in-silico subject model processes the received subject-specific parameters 25 in a first input unit 30 to derive a first input or set of inputs 32 to a computational model 34. A second input or set of inputs 36 relates to parameters of the subject which can be directly monitored, for example as obtained from a scanning system 38. The scanning system may be an ultrasound, magnetic resonance or CT imaging system. These are just examples of direct monitoring approaches.

The computational model 34 predicts the response of the subject to the actual or predicted external stimuli and thereby predict an onset of a physiological condition of the subject.

The input parameters of the computational model 34 can be geometric, mechanical or functional parameters. For example, the thickness of lining tissue, the tissue stiffness, permeability etc. The external stimuli—which can be measured with sensors—can be mechanical, chemical, thermal or optical. For example contact pressure, sliding friction, vibrations, chemical substances in the form of liquids or gases (medication, hormones, air pollution, pollen), light or thermal stimuli from device treatments, etc.

The input parameters of the computational model are in this way adapted based on the response of the in-vitro model. This can be done once (when a new digital twin is being created), intermittently, or in real time, depending on the application.

A graphical user interface 40 provides output information to the subject and/or physician. The information may be in the form of a personalized treatment advice to a physician, or feedback to a subject (e.g. instructions to adapt medication or behavior).

This system combines in-vitro monitoring and in-silico analysis. The in-vitro monitoring is used to determining the response to a tissue or organ to a particular stimuli, which may be a drug which may be administered or external atmospheric or environmental conditions to which the subject may be exposed. The in-vitro model generates parameters which cannot or are not being monitored in-vivo. These parameters supplement the actually monitored parameters of the subject when using the in-silico model to make predictions about the physiological condition of the subject. The physiological condition of the subject being predicted is for example a condition which requires medical intervention, or else preventative action to be taken.

Some possible examples of use of the system will now be described.

A first example makes use of a computational model 34 which is a "computational fluid dynamics" (CFD) simulation of air and mucus flow in the human airways, based on a subject-specific airway geometry from e.g. a CT scan. The aim of the application is to timely warn or intervene for upcoming acute events such as a lung exacerbation.

During an exacerbation the subject's lung function deteriorates rapidly due to obstructed airways, something which often occurs with Chronic Obstructive Pulmonary Disease (COPD) and asthma patients. The obstruction is often severe due to which the subject is admitted to the hospital. The airway obstruction arises from inflamed and swollen airways leading to a diameter restriction and subsequent increased air flow resistance, or from accumulated mucus due to an increased production and/or a decreased clearance.

The system is thus used to generate a model of the subject-specific nominal geometry of the airways via image segmentation (e.g. from a CT scan). The nominal geometry comprises a mapping of the airways and the local diameters of the airways in a "nominal" condition. "Nominal" refers to a reference condition of the particular subject, for example corresponding to a condition in which the lung function is manageable and stable.

The subject-specific in-vitro model is obtained in the laboratory. For example, a cell culture may be used which is based on pluripotent stem cells or tissue specific cells of the subject. Methods to build such an in-vitro model are cell culturing (Benam, K. H., et al., 2017, "Human Lung Small Airway-on-a-Chip Protocol", In: Koledova Z. (eds) 3D Cell Culture. Methods in Molecular Biology, vol 1612. Humana Press, New York, N.Y.) or 3D printing (as disclosed in US2018/0053346A1).

The laboratory makes use of experimental methods to characterize the tissue and mucus properties of the in-vitro model.

The mucus rheological parameters may be determined for example using methods disclosed by Guo, H. and Kanso, E., 2017, "A computational study of mucociliary transport in healthy and diseased environments, European journal of computational mechanics", Vol. 26, No. 1-2, pp. 4-30 and by Chatelin, R. et al., 2017, "Numerical and experimental investigation of mucociliary clearance breakdown in cystic fibrosis", Journal of Biomechanics, Vol. 53, pp. 56-63.

The mucus can be measured while still on the cell culture, or when removed from the cell culture with a rheometer. The thickness of the tissue (i.e. the wall thickness of the airways) may for example be obtained by optical methods.

The actual or predicted data relating to the external parameters of the subject will depend on the conditions being monitored, such as pollen levels, air pollution or weather conditions. The data can be acquired by sensors or from online resources such as weather, pollen and air pollution predictions.

The in-vitro model is challenged with the particular environmental conditions or other stimuli, for example pollen, air pollution (ultrafine particles, dust, smoke etc.), medications, concentrated oxygen, vibrations etc.

The variation in tissue thickness ($\Delta$) and mucus properties under the different conditions are compared to the nominal thickness. A numerical method is used to determine a subject-specific actual geometry of the airways by adapting the nominal airway diameter: (actual diameter=nominal diameter−2$\Delta$).

The computational model 34 calculates the air flow and mucus flow in the airways based on the actual airway geometry, mucus properties and inhalation flow rate (from breathing rate sensor or estimated).

Numerical methods for the simulation of mucus flow are disclosed for example by Paz, C. et al., 2017, "Glottis effects on the cough clearance process simulated with a CFD dynamic mesh and Eulerian wall film model", Computer Methods in Biomechanics and Biomedical Engineering, Vol 0.20, No. 12, pp. 1326-1338 and Paz, C. et al., 2017, "CFD transient simulation of the cough clearance process using an Eulerian wall film model", Computer Methods in Biomechanics and Biomedical Engineering, Vol. 20, No. 2, 142-152.

Numerical methods for the simulation of air flow are provided for example by De Backer, J. W. et al., 2008, "Flow analyses in the lower airways: Patient-specific model and boundary conditions", Medical Engineering & Physics 30 (2008) 872-879.

The air flow and mucus flow simulations are related in the sense that the air flow simulations deliver a boundary condition for the mucus flow simulations (i.e. local air flow velocities).

The output parameters of the computational model 34 may in this case comprise a mucus mass flow (and an analysis of whether it is stable or accumulating) and the total airway resistance (again with an analysis of whether it is stable or accumulating). A simulate may be performed for a future time period, for example one week ahead, to predict upcoming exacerbations.

In the case of an upcoming exacerbation, the effect of different interventions (medication type/dose, vibration vest, oxygen supplementation, mechanical ventilation) may be simulated, and feedback may then be provided on the most effective intervention.

A second example is for monitoring organ function, such as the kidney, liver, prostate, bladder, ovaries, eye, skin, arteries, mouth (gums, saliva, biofilm) etc.

The in-vitro model may comprise a multi-organ model. For example a combination of kidney and liver tissue interacting ("communicating") with each other via chemicals transported in microfluidic channels. The interaction can be modulated in the manner explained above for the feedback system A third example is for prediction of the cardiac output. The cardiac output of the heart is determined by the geometry of the heart, the contraction power of the heart muscle cells and the heart rhythm. These parameters can be used as the inputs for the in-silico heart biophysical model to calculate the pressure-volume loop and derive the cardiac output which is a relevant clinical parameter to diagnose a subject. Although the cardiac output can be measured by a catheter, it may be not desirable to use this intervention on often very sick patients.

The geometry can be conveniently determined by an imaging modality, but the contraction power of the heart muscle cells is difficult to assess. A culture of subject heart cells, via IPC stem cells, may be generated and contractility is measured as function of external stimuli. In this case, the stimuli are electrophysiological events. For example, an electrical stimulation of the cells with a frequency equal to the frequency of the heart rate of the subject may be used. Also, irregular frequency stimulation can be used simulating an irregular heartbeat of the subject. Even the in-vitro cells can be challenged over time.

In all examples above, the subject may also be able to input to the system, via the graphical user interface, if the actual status corresponds to the simulated status. This enables a self-learning function of the computational model.

A feedback system may be also implemented to enable a proactive approach for determining an optimal intervention and/or for improving the reliability of the treatment advice. This may involve modulating the input parameters of the in-vitro model using positive stimuli (e.g. medication intervention) and negative stimuli (e.g. pollutant particles).

The response of the in-silico model may then be evaluated to determine how to bring the in-vitro system—which is specific to the patient—to a stable condition. In this way, the in-silico model is used to predict the effect of input parameters on the in-vitro model, and on the basis of these predicted effects, instructions are derived of how to modulate the input parameters for the in-vitro model.

The response of the in-vitro model is subsequently fed back into the in-silico model thereby implementing a feedback system. The in-silico model is updated and makes a new prediction and the cycle starts again until the in-vitro system is in the desired stable condition. When the in-vitro system is stable, the intervention can then be applied to the real patient.

In this way, the in-vitro and in-silico models run sequentially. This approach is useful with time-dependent input-output relations, for example when dose-response relationships are involved (e.g. pharmacokinetic/pharmacodynamics models).

In a modification, population data may be used as well as individual subject information. For example, the in-vitro contractility in various systems may be used. A population of subjects may be analyzed to establish a population average of the contractility as function of various stimuli. This can lead to a more precise relationship between the stimuli and the contractility, by averaging out randomness of certain (unknown) noise sources. The electrophysiological events of a subject may be used as input to a look up table, which then translates this into a contractility of the muscle cells, and subsequently the in-silico model uses amongst others the contractility to calculate the cardiac output.

Figure 2:
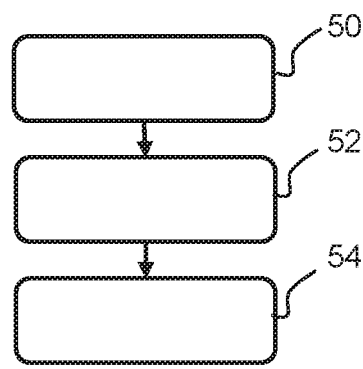
FIG. 2 shows a method for predicting the onset of a physiological condition of a subject.

FIG. 2 shows method for predicting the onset of a physiological condition of a subject, comprising:

in step 50, using an in-vitro subject model for modeling a tissue or organ type of a subject based on sample cells from the subject, the in-vitro model comprising input parameters relating to actual or predicted external stimuli to which the subject is or may be exposed;

in step 52, outputting subject-specific parameters of the subject from the in-vitro subject model which are not being monitored, or cannot be monitored, in-vivo; and in step 54, using an in-silico subject model comprising subject-specific data which is relevant for the response of the particular subject to the subject-specific parameters, wherein the in-silico subject model is used to process the subject-specific parameters thereby to predict the response of the subject to the actual or predicted external stimuli and thereby predict an onset of a physiological condition of the subject.

From the examples above, it can be seen that the subject-specific parameters of the in-vitro subject model for example comprise one or more of:

a tissue thickness;
an amount of stretching of tissue in response to an applied pressure;
a tissue stiffness; and
a contraction power of muscle tissue.

The input parameters to the in-vitro subject model for example comprise one or more of:

exposure to a medicinal drug;
exposure to pollutants;
exposure to pressure;
exposure to particular concentrations of oxygen; and
exposure to vibration.

The scan data may comprise one or more of:
the airway geometry; and
the geometry of an organ of the subject.

The invention is of interest for predicting allergic reactions or asthma episodes, for generating personalized medicine recommendations, and for risk prediction.

The computational model of the in-silico model is implemented by a controller, which can be implemented in numerous ways, with software and/or hardware, to perform the various functions required. A processor is one example of a controller which employs one or more microprocessors that may be programmed using software (e.g., microcode) to perform the required functions.

A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for predicting a response of a subject to external stimuli, comprising:
    an in-vitro subject system for modeling a tissue type or organ type of the subject based on sample cells from the subject, the in-vitro system comprising input parameters relating to actual or predicted external stimuli to which the subject is or may be exposed, wherein the in-vitro system is adapted to output, using the input parameters, subject-specific parameters which are not being monitored, or cannot be monitored, in-vivo, wherein the in-vitro subject system comprises a microfluidic system; and
    a processor separate from the microfluidic system and comprising an in-silico subject model, the in-silico model comprising subject-specific data which is relevant for the response of the particular subject to the subject specific parameters, wherein the in-silico subject model is adapted to process the subject-specific parameters thereby to predict the response of the subject to the actual or predicted external stimuli.

2. A system as claimed in claim 1, wherein the subject-specific parameters of the in-vitro subject system comprise one or more of:
    a tissue thickness;
    an amount of stretching of tissue in response to an applied pressure;
    a tissue stiffness; and
    a contraction power of muscle tissue.

3. A system as claimed in claim 1, wherein the input parameters to the in-vitro subject system comprise one or more of:
- exposure to a medicinal drug;
- exposure to pollutants;
- exposure to pressure;
- exposure to particular concentrations of oxygen; and
- exposure to vibration.

4. A system as claimed in claim 1, comprising a sensor arrangement for providing sensor information, or an input for receiving sensor information from a remote source, wherein the sensor information is provided to the in-vitro subject system.

5. A system as claimed in claim 1, wherein the subject-specific data of the in-silico subject model comprises scan data.

6. A system as claimed in claim 5, wherein the scan data comprises one or more of:
- the airway geometry; and
- the geometry of an organ of the subject.

7. A system as claimed in claim 1, wherein the in-silico subject model is further adapted to derive treatment recommendations.

8. A system for predicting a response of a subject to external stimuli, comprising:
- a microfluidic system comprising sample cells from the subject, wherein the microfluidic system is configured to generate, based on one or more received input parameters relating to external stimuli to which the subject is or may be exposed, one or more subject-specific parameters which are not being monitored, or cannot be monitored, in-vivo for the subject;
- a processor separate from the microfluidic system and comprising an in-silico subject model, the in-silico model comprising subject-specific data which is relevant for a response of the particular subject to the subject-specific parameters, wherein the in-silico subject model is configured to process the subject-specific parameters to predict the response of the subject to the actual or predicted external stimuli.

9. The system of claim 8, further comprising:
- a sensor arrangement configured to obtain sensor information, wherein the sensor information is provided to the microfluidic system, and wherein the input parameters relating to the external stimuli to which the subject is or may be exposed are based on the sensor information.

10. The system of claim 8, wherein:
- the input parameters provided to the microfluidic system comprise one or more of exposure to a medicinal drug, exposure to a pollutant, exposure to pressure, exposure to a particular concentration of oxygen, and exposure to vibration; and
- the subject-specific parameters generated by the microfluidic system comprise one or more of a tissue thickness, an amount of stretching of tissue in response to an applied pressure, a tissue stiffness, and a contraction power of muscle tissue.

11. The system of claim 8, wherein the subject-specific data of the in-silico subject model comprises scan data, the scan data comprising one or more of the airway geometry, and the geometry of an organ of the subject.

* * * * *